(12) United States Patent
Riley et al.

(10) Patent No.: US 7,973,206 B1
(45) Date of Patent: Jul. 5, 2011

(54) ALKYLATION PROCESS USING CATALYSTS WITH LOW OLEFIN SKELETAL ISOMERIZATION ACTIVITY

(75) Inventors: Mark G. Riley, Hinsdale, IL (US); Deng-Yang Jan, Elk Grove Village, IL (US); Stephen W. Sohn, Arlington Heights, IL (US); Jaime G. Moscoso, Mount Prospect, IL (US)

(73) Assignee: UOP LLC, Des Plaines, IL (US)

( * ) Notice: Subject to any disclaimer, the term of this patent is extended or adjusted under 35 U.S.C. 154(b) by 33 days.

(21) Appl. No.: 12/639,971

(22) Filed: Dec. 16, 2009

(51) Int. Cl.
*C07C 2/66* (2006.01)
(52) U.S. Cl. ........................................ 585/467; 585/455
(58) Field of Classification Search .................. 585/467, 585/455
See application file for complete search history.

(56) References Cited

U.S. PATENT DOCUMENTS

| | | | |
|---|---|---|---|
| 4,301,317 A | 11/1981 | Young | |
| 6,133,492 A | 10/2000 | Anantaneni | |
| 6,521,804 B1 | 2/2003 | Marinangeli et al. | |
| 6,756,030 B1 | 6/2004 | Rohde et al. | |
| 6,977,319 B2 | 12/2005 | Campbell et al. | |
| 7,091,390 B2 | 8/2006 | Jan et al. | |
| 7,268,267 B2 | 9/2007 | Jan et al. | |
| 7,297,826 B2 | 11/2007 | Joly et al. | |

FOREIGN PATENT DOCUMENTS

WO  WO 2009/071709 A1  6/2009

OTHER PUBLICATIONS

U.S. Appl. No. 12/639,973, filed Dec. 16, 2009, Riley et al.
U.S. Appl. No. 12/639,596, filed Dec. 16, 2009, Jan et al.
U.S. Appl. No. 12/639,968, filed Dec. 16, 2009, Jan et al.
Gee et al., A Kinetic and mechanistic study of the double bond and skeletal isomerization of 1-tetradecene on SAPO-11, Applied Catalysis A: General 360 , 71-80, (2009).
Peterson et al., , Hydroisomerization of Normal Olefins under Alkylation Conditions, I&EC Product & Research Dev., 4, No. 4, 261-265 (1965).
Venuto et al., Organic Reactions Catalyzed by Crystalline Aluminosilicates, Journal of Catalysis, 5, 81-98, 87 (1966).
Deshumkh et al., Alkylation of benzene with long chain (C8-C18) linear primary alcohols over zeolite-Y, Catalysis Letters 64, 247-250 (2000).
Galinski, et al., Alkylation of benzene by α-olefins on modified faujasite, Petroleum Chemistry vol. 35, 2, pp. 143-146 (1995).
He et al., Liquid phase alkylation of benzene with propylene over large pore zeolite catalysts, Jour. of Fuel Chem & Tech. 27(3) p. 203-208, Chinese (English Abstract), (1999).
Meriaudeau et al., Zeolite based catalysts for linear alkylbenzene production: Institut de Recherches, Elsevier Catalysis Today 38, p. 243-247 (1997).
Minachev et al., New Application of Zeolite Systems in Catalitic Organic Syntheses, Inst. of Organic Chem., Moscow, 1989 Elsevier Science, p. 47 (1989).
Sivasanker et al., Shape Selective Alkylation of Benzene with Long Chain Alkenes over Zeolites, 10th Intl Congress of Catalysis, Budapest, Hungary (1992).
Thomas et al., Towards a Green Synthesis of LAB's: Effect of Rare Earth Metal Ions on the Benzene Alkylation . . . , Journal of Mater Sci 41, p. 1611-1616, (2006).
Thomas et al., Alkylation of Benzene with 1-octene over rare earth exchanged HFAU-Y Zeolites, Reaction Kinetics and Cat. Ltrs, V85, 1, p. 29-36 (2005).
Kovacheva et al., Oxidative methylation of toluene with methane using X zeolite catalyst . . . , Applied Catalysis A: General 223, p. 121-128 (2002).
Madhavi et al., Side-Chain Alkylation of Heterocyclic Compounds over Modified Zeolites, Studies in Surface Science & Cat. v 154, p. 2760-2766 (2004).
Ono et al., Selective reactions over solid base catalysts, Tokyo, Japan, Catalysis Today, 38 p. 321-337 (1997).
Wang, Lee, Cai, Park., Benzene alkylation with 1-dodecene over H-mordenite zeolite, Catalysis Letters, V 76, No. 1-2, (2001).
Yu, Sidorenko, Galich, Selective Alylation of Methyl-Substituted Aromatic Hydrocarbons on Acid and Basic Zeolites, Petrol. Chem V31, p. 57-69 (1991).
Vasil'Ev et al., Catalysts of obtaining styrene and its derivatives, Khimiya i Teknologiya Topliv I Masel—1997_MT_Eng (in Russian).
Vasil'Ev et al., Catalysts of obtaining styrene and its derivatives, Khimiya i Teknologiya Topliv I Masel—1997_MT_Eng (in English).
Wieland et al., Side-Chain Alkylation of Toluene with Methanol over Alkali-Exchanged Zeolites X, Y, L, and β, Jour. of Catalysis, 173, 490-500 (1998).
Zeng, Study on a New Technology of p-Nitrobenzoic Acid Production, Shiyou Huagong Petro. Technology (1999), Chinese with English Abstract.

*Primary Examiner* — Thuan Ding Dang
(74) *Attorney, Agent, or Firm* — Arthur E Gooding

(57) ABSTRACT

A process is presented for the production of linear alkylbenzenes. The process includes contacting an aromatic compound with an olefin in the presence of a selective zeolite catalyst. The catalyst includes two zeolites combined to improve the linearity, and to produce detergent grade LAB. The two zeolites are selected to limit skeletal isomerization while producing a desired 2-phenyl content for the LAB.

3 Claims, 1 Drawing Sheet

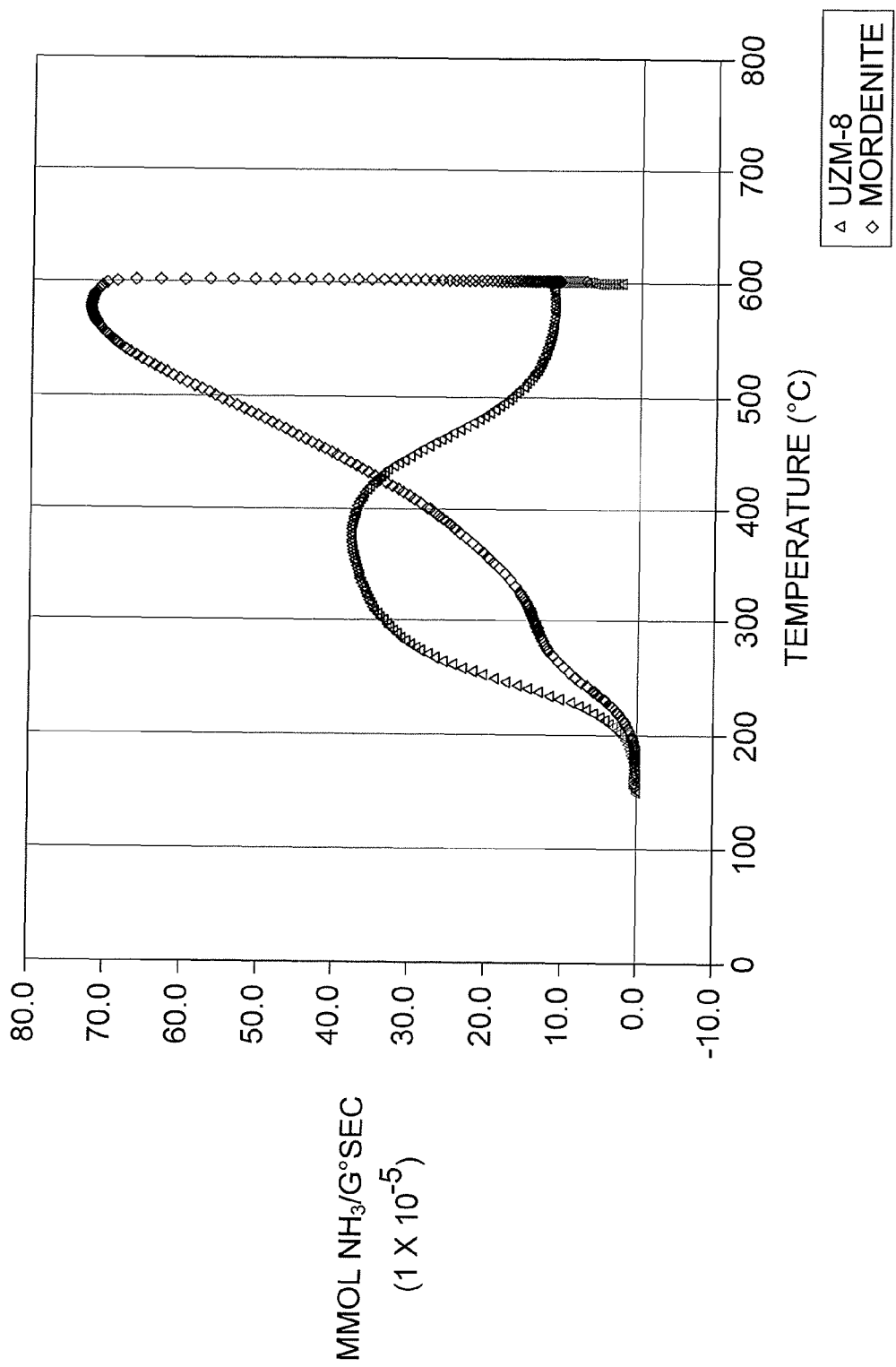

ALKYLATION PROCESS USING CATALYSTS WITH LOW OLEFIN SKELETAL ISOMERIZATION ACTIVITY

FIELD OF THE INVENTION

The present invention is directed to highly selective, modified catalysts and the process of using the catalysts. The catalysts are for use in the alkylation of aromatic compounds.

BACKGROUND OF THE INVENTION

Alkylation of benzene produces alkylbenzenes that may find various commercial uses, e.g., alkylbenzenes can be sulfonated to produce surfactants, for use in detergents. In the alkylation process, benzene is reacted with an olefin the desired length to produce the sought alkylbenzene. The alkylation conditions comprise the presence of homogeneous or heterogeneous alkylation catalyst such as aluminum chloride, hydrogen fluoride, or zeolitic catalysts and elevated temperature.

Various processes have been proposed to alkylate benzene. One commercial process involves the use of hydrogen fluoride as the alkylation catalyst. The use and handling of hydrogen fluoride does provide operational concerns due to its toxicity, corrosiveness and waste disposal needs. Solid catalytic processes have been developed that obviate the need to use hydrogen fluoride. Improvements in these solid catalytic processes are sought to further enhance their attractiveness through reducing energy costs and improving selectivity of conversion while still providing an alkylbenzene of a quality acceptable for downstream use such as sulfonation to make surfactants.

Alkylbenzenes, to be desirable for making sulfonated surfactants must be capable of providing a sulfonated product of suitable clarity, biodegradability and efficacy. With respect to efficacy, alkylbenzenes having higher 2-phenyl contents are desired as they tend, when sulfonated, to provide surfactants having better solubility and detergency. Thus, alkylbenzenes having a 2-phenyl isomer content in the range from about 30 to about 40 percent are particularly desired.

Improvements in the catalysts have facilitated the production of linear alkylbenzenes, as shown in U.S. Pat. No. 6,133, 492, U.S. Pat. No. 6,521,804, U.S. Pat. No. 6,977,319, and U.S. Pat. No. 6,756,030. However, problems exist with many existing catalysts, and a better understanding, can lead to further improvements in the catalysts.

SUMMARY OF THE INVENTION

The present invention provides for a process for producing a monoalkylated aromatic compound having an increased linearity of the alkyl group. The process comprises reacting an aromatic feedstock with an olefinic compound in an alkylation reactor at reaction conditions using a catalyst comprising two zeolites.

The first zeolite comprising a microporous crystalline zeolite having a layered framework of at least $AlO_2$ and $SiO_2$ tetrahedral units and a composition on an as-synthesized and anhydrous basis expressed by an empirical formula of:

$$M_m^{n+} R_r^{p+} Al_{1-x} E_x Si_y O_z$$

where M is at least one exchangeable cation selected from the group consisting of alkali and alkaline earth metals, "m" is the mole ratio of M to (Al+E) and varies from 0 to about 2.0, R is at least one organoammonium cation selected from the group consisting of quaternary ammonium cations, diquaternary ammonium cations, protonated amines, protonated diamines, protonated alkanoamines and quaternized alkanolammonium cations, "r" is the mole ratio of R to (Al+E) and has a value of about 0.05 to about 5.0, "n" is the weighted average valence of M and has a value of about 1 to about 2, "p" is the weighted average valence of R and has a value of about 1 to about 2, E is an element selected from the group consisting of gallium, iron, boron, chromium, indium and mixtures thereof, "x" is the mole fraction of E and has a value from 0 to about 1.0, "y" is the mole ratio of Si to (Al+E) and varies from about 6.5 to about 35 and "z" is the mole ratio of O to (Al+E) and has a value determined by the equation:

$$z=(m \cdot n+r \cdot p+3+4 \cdot y)/2.$$

The catalyst further includes a second zeolite having a silica to alumina molar ratio less than 4.8, and wherein the second zeolite has a rare earth element incorporated into the zeolitic framework in an amount greater than 16.5 wt %. The first and second zeolites are intermingled into single catalyst particles, where the first zeolite is in an amount between 10 and 90% by weight of the catalyst, and the second zeolite component is in an amount between 10 and 90% by weight.

In one embodiment, the first zeolite is UZM-8, and the second zeolite is a rare earth substituted X or Y zeolite.

Other objects, advantages and applications of the present invention will become apparent to those skilled in the art from the following drawing and detailed description.

BRIEF DESCRIPTION OF THE DRAWING

FIGURE is the ammonia desorption from UZM-8 and mordenite.

DETAILED DESCRIPTION OF THE INVENTION

The alkylation of aromatics with olefins in important for several commercially important technologies. Ethyl benzene (EB), cumene (isopropyl benzene), and larger chained alkylbenzenes (detergents) are the three most economically important examples. The detergents preferably made using longer chained linear alkyl groups, such as C8 to C16, to form linear alkyl benzenes (LAB). These alkylation reactions are carried out using acid catalysts, either homogeneous catalysts such as HF, or heterogeneous catalyst such as $AlCl_3$, silica-alumina, and zeolites. Although these are all acid catalyzed processes, there are enough differences that they are all practiced with different catalysts. Skeletal isomerization is an example of a concern in the LAB process, and which makes the use of catalysts suitable for EB or cumene of less value in the LAB process.

The production of linear alkylbenzenes has traditionally been made in two commercial forms, low 2-phenyl and high 2-phenyl. Low 2-phenyl LAB is made by HF alkylation and results in a 2-phenyl concentration between 15 and 20 mass percent of the LAB. This is due to the homogeneous acid, HF, lack of preference for catalyzing the attachment of the benzene to the olefin chain. There is not alkylation on the terminal carbons, and the internal carbons have a nearly equal probability of alkylation, and which produces shorter chained alkyl groups extending from the benzene. High 2-phenyl LAB has historically been made using $AlCl_3$ alkylation and results in a 2-phenyl concentration between 30 and 35 mass percent of the LAB. While it is possible to produce LAB with different 2-phenyl contents, there is no market for these products, and consequently the efforts have been to replace these environmentally unfriendly catalysts.

In 1995, UOP and Cepsa introduced a detergent alkylation process using the first environmentally friendly solid bed alkylation process for the production of LAB. The catalyst was a fluorided silica-alumina catalyst, and the process produces a high 2-phenyl LAB product. This process has nearly completely replaces the use of AlCl₃ in detergent alkylation. However, it uses considerably more energy than the HF process due to the much higher benzene to olefin ratio in the process, and produces slightly more dialkylate than the HF process.

While ethylbenzene, cumene and LAB are all produced in processes using acid catalysts, there are a number of key features that differentiate LAB from either ethylbenzene or cumene. One is the length of the olefin and the reactions that the olefin can undergo. Solid acid catalysts are known to catalyze both double bond isomerization and skeletal isomerization in linear olefins. Most studies of double bond and skeletal isomerization of linear olefins has focused on 1-butene. This is due to the desire to make isobutene for MTBE, an oxygenate for gasoline, or polyisobutene. Gee and Prampin, *Applied Catalysis A: General* 360 (2009), 71-80. Even a weak acid catalyst, like SAPO-11, produces skeletal isomerization, and is easily observed at 142 C, and that skeletal isomerization is temperature dependent.

It is known that skeletal isomerization of linear olefins occurs in the production of LAB over solid acid catalysts. In 1965, in an article titled "Hydroisomerization of Normal Olefins Under Alkylation Conditions" showed that skeletal isomerization was favored by high acid concentrations and high temperatures (Peterson, A. H., Phillips, B. L., and Kelly, J. T., *I&EC*, 4, No. 4, 261-265, 1965). Also, as shown in U.S. Pat. No. 4,301,317 to Young, Table 2 compares the amount of linear phenyldodecane produced by alkylation of 1-dodecene with benzene over eight different zeolites. All of the zeolites exhibited skeletal isomerization. Inhibiting skeletal isomerization is an important challenge to be addressed, if one is to produce highly linear detergent range alkylbenzenes. It is further worth noting that Beta zeolite, which is commonly used in the production of ethylbenzene and cumene is unsuitable for detergent range LAB production due to its tendency to skeletally isomerizes the linear olefins prior to their alkylation. Because ethylene and propylene only have one isomer, both the double bond and skeletal isomerization of the catalyst are moot and for this reason one cannot predict that a process or catalyst for ethylbenzene or cumene production will necessarily extend to LAB.

A second difference between alkylation of long chain linear olefins with benzene differs from that of ethylbenzene or cumene is the number of products. Ethylbenzene and cumene are unique chemical compounds whereas LAB is a mixture of compounds that results from the fact that long chain linear olefins have multiple positions for the benzene to insert itself. As can be seen from Young's data in U.S. Pat. No. 4,301,317, molecular sieves can reduce or prohibit the formation of some phenylalkane isomers. This is phenomena is called shape selectivity and occurs because the molecular sieve doesn't possess enough space for the molecule to be formed. Since the commercially desirable detergent range linear alkylbenzenes, "low 2-phenyl LAB" and "high 2-phenyl LAB" have relative narrow windows on their 2-phenylalkane content, an acidic molecular sieve catalyst that has good characteristics for producing ethylbenzene or cumene cannot be assumed to be appropriate for producing commercially acceptable detergent range LAB.

A third way in which the alkylation of long chain linear olefins with benzene differs from that of ethylbenzene or cumene is in the impact of the benzene to olefin ratio. Alkylation processes to convert ethylene to ethylbenzene and propylene to cumene operate at significantly low benzene to olefin ratios than solid detergent alkylation processes. It has long been known that monoalkylate selectivity can be maximized by operating at high benzene to olefin ratios. High benzene to olefin ratios also means the ratio of benzene to monoalkylate is high and the higher the weight fraction of benzene relative to other aromatics, the higher the yield of monoalkylate. In the production of ethylbenzene or cumene low benzene to olefin ratios can be employed to minimize energy usage because the polyethylbenzene or polypropylbenzene can be easily transalkylated with benzene to produce the desired product, ethylbenzene or cumene. In the detergent alkylation process, where a solid fluorided amorphous silica-alumina catalyst is employed, shape selectivity does not come into play due to the very large pores and the only way to control the amount of dialkylbenzene is to use high benzene to olefin ratios. Converting long chain linear dialkylbenzenes back to long chain linear monoalkylbenzenes can be done, but with significantly lower efficiency than for ethylbenzene or cumene. Some of the transalkylation occurs though dealkylation followed by alkylation with benzene. When transalkylation occurs through this pathway some of the olefin undergoes skeletal isomerization, which lowers overall product linearity.

Low benzene to olefin ratios also promotes the skeletal isomerization of linear olefins. Because skeletal isomerization is a monomolecular reaction and alkylation is a bimolecular reaction, lowering the benzene to olefin ratio effectively increases the olefin concentration which causes the rate of olefin skeletal isomerization to increase faster than the rate of olefin alkylation. Thus, in solid detergent alkylation processes, one is faced with the choice of operating at high benzene to olefin ratios and accepting the high energy cost or finding catalysts with the appropriate acidity such that skeletal isomerization of the linear olefins is minimal.

It is possible to adjust the 2-phenyl content of detergent range LAB by physically blending a first product produced with a first alkylation catalyst that produces a product rich in 2-phenylalkanes and a second product with a second alkylation catalyst that produces a product lean in 2-phenylalkanes. The blend can be accomplished in any number of ways including separate tankage, by controlling the amount of olefin going to each alkylation catalyst reaction zone, or by using a physical mixture of two catalyst in the same reaction zone. In U.S. Pat. No. 6,133,492, Anantaneni proposed using fluorided mordenite as the "rich" 2-phenyl catalyst and AlCl3, fluorided clay, or silica-alumina as the "lean" 2-phenyl catalyst. Anantaneni disclosed both physical mixtures and distinct catalyst beds in series. This was improved upon by replacing the "lean" 2-phenyl components with zeolites that are much more selective to mono-alkylbenzene than AlCl3, fluorided clay or silica-alumina, as shown in U.S. Pat. No. 7,297,826, by Joly and Briot. The improvement allows the production of more mono-alkylbenzene at similar benzene to olefin ratios or to produce the same amount of mono-alkylbenzene while less energy due to lower benzene to olefin ratios.

From an operations point of view it is desirable to use a single catalyst. With multi-catalyst systems one has to be concerned about differing rates of deactivation, regeneration, and long term stability. In addition, there is segregation of catalysts within a reactor when there are more than one type of catalyst from a physical mixture. The segregation can occur during the loading, or in the case of a fluidized bed system, through the movement of the catalyst particles.

Therefore, when having two catalysts in a reactor, it is desirable to have the two catalysts intermingled in a single catalyst particle.

Single catalyst alkylation processes are no more complex than those based on AlCl3 or fluorided silica-alumina. Because detergent range LAB is a chemical intermediate, a catalyst system will need to produce LAB that conforms to the existing commercial specifications. Meeting all of these LAB product specifications imposes a number of constraints on the formulation of the catalyst. Among the constraints that are critical are:
1) 2-phenylalkane content
2) Olefin isomerization activity
3) Deactivation rate
4) Regenerability
5) Limited change in LAB product quality as the catalyst ages To overcome the drawbacks of mixtures of catalysts, the present invention comprises a catalyst for the alkylation of aromatics comprising a first zeolite for producing a "rich" 2-phenyl content and a second zeolite for producing a "lean" 2-phenyl content. The first zeolite comprising a microporous crystalline zeolite having a layered framework of at least AlO2 and SiO2 tetrahedral units and a composition on an as-synthesized and anhydrous basis expressed by an empirical formula of:

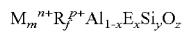

$$M_m^{n+}R_r^{p+}Al_{1-x}E_xSi_yO_z$$

where M is at least one exchangeable cation selected from the group consisting of alkali and alkaline earth metals, "m" is the mole ratio of M to (Al+E) and varies from 0 to about 2.0, R is at least one organoammonium cation selected from the group consisting of quaternary ammonium cations, diquaternary ammonium cations, protonated amines, protonated diamines, protonated alkanoamines and quaternized alkanolammonium cations, "r" is the mole ratio of R to (Al+E) and has a value of about 0.05 to about 5.0, "n" is the weighted average valence of M and has a value of about 1 to about 2, "p" is the weighted average valence of R and has a value of about 1 to about 2, E is an element selected from the group consisting of gallium, iron, boron, chromium, indium and mixtures thereof, "x" is the mole fraction of E and has a value from 0 to about 1.0, "y" is the mole ratio of Si to (Al+E) and varies from about 6.5 to about 35 and "z" is the mole ratio of O to (Al+E) and has a value determined by the equation:

$$z=(m \cdot n + r \cdot p + 3 + 4 \cdot y)/2.$$

The second zeolite having a silica to alumina molar ratio less than 8, and includes a rare earth element incorporated into the zeolitic framework in an amount greater than 16.5 wt %. The first zeolite component is in an amount between 10 and 90% by weight of the catalyst, and the second zeolite component is in an amount between 10 and 90% by weight. The zeolites are intermingled into single catalyst particles.

The zeolites are mixed and produced to have two zeolites within a single catalyst pellet. A preferred ratio of the first zeolite to the second zeolite is between 1:4 and 3:4.

The first zeolite is UZM-8 and is a zeolite that is particularly well suited as the "rich" 2-phenyl component. Although UZM-8 has some similarities with layered microporous crystalline materials, there are differences in structure and composition, as presented in U.S. Pat. No. 6,756,030 to Rohde et al., and is incorporated by reference in its entirety. LAB produced using UZM-8 has a 2-phenyl content between 40 and 50 weight percent. UZM-8 is rich in moderate strength, easily accessed acid sites. This topology minimizes olefin isomerization, cracking and the rate of catalyst deactivation. Compared to mordenite, which has fairly strong acidity, UZM-8 is much less prone to isomerization or cracking of the olefins before alkylation. The differences in acid site strength distribution between UZM-8 and mordenite are clearly observable using NH4 TPD. In the FIGURE, approximately 40% of the NH3 desorbs from UZM-8 between 400 and 550° C., but in mordenite the amount of NH3 desorbing in the same temperature range is roughly 70% of the total. Other zeolites that meet the desired characteristics include PSH-3, SSZ-25, MCM-22, MCM-49 and MCM-56. The first zeolite is also characterized by its acidity, wherein the acidity is characterized by having less than 70% of NH3 desorption off the zeolite at temperatures greater than 400° C.

The NH3-TPD experimental procedure comprises: calibration of the NH3-TPD system with 5 injections of 0.2 cc pulses of NH3 at 2 minute intervals into a flow of UHP grade helium at 40 cc/minute. The data collected from the Thermal Conductivity Detector is integrated and used to calibrate the detector response to a known quantity of NH3. An equilibrated sample, for moisture content is weighed at approximately 250 mg and placed in the reactor. The sample is pretreated in a flow of 20% O2/He UHP grade at a rate of 100 cc/minute and with a temperature ramp of 10° C./minute up to a maximum temperature of 650° C. The sample is held at this temperature for one hour, then purged with UHP grade helium for 15 minutes and cooled to the saturation temperature. The pretreatment is for removal of water and residual contaminants. The sample is saturated with anhydrous NH3 at 150° C. using multiple pulses of NH3 injected into He flowing at 40 cc/min. The minimum quantity of NH3 used to saturate the sample is 50 cc. The excess ammonia is purged from the sample in flowing (40 cc/min) UHP grade helium for ~8 hours. The NH3 is desorbed from the sample in a flow (40 cc/min) of UHP grade helium with a temperature ramp of 10° C./minute to a final temperature of about 605° C. All gases have been purified using appropriate gas purifiers. The NH3 desorbed is detected with a Thermal Conductivity Detector. The detector response is converted to moles of NH3 using the detector response obtained at the beginning of the experiment. The integrated results are reported by integration of the temperature range of interest and reported as mmoles NH3/g sample.

The second zeolite is a rare earth substituted X zeolite, Y zeolite, or a zeolite having an EMT/FAU intergrowth. The incorporation of rare earth exchanged ions in a low ratio zeolite reduces the acidity due to an increase in the number of framework alumina at low ratios, and also reduces geometric space in the supercage. The reduced acidity and reduced space significantly suppresses the isomerization and cracking pathways, while the leaving the primary alkylation reaction unaffected. This decreases the undesired side reactions that reduce the amount and quality of the LAB product. This is contrary to what one would expect, as it has been found that incorporating or leaving some alkali or alkaline earth cations in the catalyst significantly improves the catalyst performance. This is especially true with respect to the performance around the linearity of the alkylbenzene, and the retention of linearity as the operating temperatures are increased. Normally, the alkali or alkaline earth cations are removed because without the rare earth exchange, the alkali or alkaline earth cations are detrimental to the catalyst life and regenerability. A benefit of the new catalyst is an increase in the linearity of the alkylbenzene for use in detergents.

Combining the second rare earth substituted zeolite with UZM-8 in the correct proportions yields a single catalyst capable of producing "on specification" LAB with respect to the 2-phenylalkane content and with exceptional linearity.

The resulting catalyst exhibits little change in 2-phenyl content or linearity over a cycle. The catalyst is stable over time and easily regenerated by benzene wash. Placing all of the zeolite components within a single particle in the desired ratio eliminates any potential for catalyst segregation and selective deactivation of one of the components due to its position in the reactor, and it can be used as a one to one replacement for existing solid detergent alkylation catalysts.

While the sodium, Na, form of either the X or Y zeolite is inactive for benzene alkylation, the zeolites must be exchanged with less basic cations to impart catalytic activity. H-Y and US-Y are both very active for alkylation, but their high acidity is a problem with respect to linearity of the LAB produced due to olefin isomerization. Skeletal isomerization can be reduced by exchanging the Na cations with rare earth (RE) cations. RE-X and RE-Y are active for benzene alkylation, and the acid sites of RE-X and RE-Y are less acidic than those of H-Y. This yields a higher linearity. In addition, it has been found that the substitution of Na should not be complete, but some of the Na should be left behind. Too much Na and the zeolite loses activity; too little and one creates some strong acid sites that increase olefin isomerization. In general, Y zeolites with RE content greater than 16.5 weight percent and with the remaining cations being alkali and alkali earth elements or basic amines have an optimal balance of activity, selectivity and linearity. The Na contents greater than 0.3 weight percent are optimal for minimizing olefin isomerization. For cations other than Na the weight percent is based on an equal number of equivalents.

The rare earth elements selected for cation exchange include one or more of the following: scandium (Sc), yttrium (Y), lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thullium (Tm), ytterbium (Yb), and lutetium (Lu). Preferred rare earth elements include yttrium (Y), lanthanum (La), cerium (Ce), praseodymium (Pr), neodymium (Nd), gadolinium (Gd), dysprosium (Dy), erbium (Er), and ytterbium (Yb). The rare earth cations are preferably exchanged to the extent that the resulting rare earth element to aluminum atomic, or molar, ratio is in the range from 0.55 to 1.2. It is preferred that the balance of cation exchange is with alkali or alkaline earth cations for controlling the acidity of the zeolite.

The molar ratio of the silica to alumina for a rare earth substituted Y zeolite is less than 8, with a preferred ratio less than 3, and a more preferred ratio between 2.8 and 4. The molar ratio of the silica to alumina for a rare earth substituted X zeolite is less than 8, a preferred ratio less than 4, a more preferred ratio less than 2.8, and with a most preferred ratio between 2 and 2.8.

The amount and choice of the first zeolite is selected for yielding a 2-phenyl content of less than 60 mole % of the LAB produced by the final two zeolite catalyst.

The new catalyst is for use in the selective alkylation of an aromatic compound, with the process including contacting the aromatic compound with an olefin having from 8 to 16 carbon atoms in the presence of a selective zeolite catalyst at reaction conditions, wherein the selective zeolite catalyst comprises a zeolite mixture, the zeolite mixture comprising a first zeolite having a UZM-8 content between 10 and 90% by weight, a second zeolite comprising a rare earth substituted X or Y zeolite, and comprising an amount between 10 and 90% by weight. The second zeolite preferably has a rare earth element incorporated into the second zeolitic framework in an amount greater than 16.5 wt %. For detergent alkylation, the aromatic compound is benzene. The desired olefins are normal, or linear, olefins, and lightly branched olefins such as monomethyl olefins.

The catalyst can further include a binder wherein the binder comprises a clay having alumina, magnesium silicates, magnesium aluminum silicates, attapulgite, and mixtures thereof. The binder provides hardness to the catalyst to improve the physical durability of the catalyst from abrasion during operation.

The alkylation process is temperature dependent with increasing temperature generally increasing the amount of skeletal isomerization. The process is operated to obtain a controlled yield, with the temperature increased as the catalyst ages before regenerating the catalyst. The new catalyst minimizes skeletal isomerization at higher temperatures. The end of the useful life of a catalyst is often when the amount of isomerization is sufficient to produce an LAB with a linearity that is meet a detergent manufacturer's specification. Reducing the amount of skeletal isomerization increases the useful life of the catalyst. The process is operated at a temperature between 80° C. and 200° C., and preferably at a temperature between 100° C. to 160° C. Other reaction conditions include operating at pressures to maintain the reactants in the liquid phase. The alkylation reactor is operated at a pressure between 1300 kPa and 7000 kPa, and preferably at a pressure is between 2500 and 4500 kPa.

The catalyst in the process uses a second zeolite that has a low silica to alumina ratio and is an X or Y zeolite that has been cation exchanges with a rare earth element.

Experiments were run using several zeolite combinations. Presented here are two of the combinations that show one needs to have a careful selection of zeolites, and the choices are not obvious.

A first catalyst of the invention was chosen comprising 24% UZM-8, 56% RE-Y, and 20% alumina binder and is formed as a $\frac{1}{16}$" extrudate using ordinary techniques. A second catalyst was chosen, for comparison with the invention, comprising of 24% MOR, 56% RE-Y, and 20% alumina binder and is formed as a $\frac{1}{16}$" extrudate using ordinary techniques. These are similar catalysts, except for the choice of the first zeolite. The catalysts were tested in a plug flow reactor using a feedstock of C10 to C13 n-olefins and n-paraffins blended with sufficient benzene to make the benzene to olefin molar ratio equal to approximately 10. Equal volumes of catalyst were used in the testing, and the temperature was adjusted to obtain a high olefin conversion as measured by the Bromine Index.

The testing process followed a two day cycle with a 24 hour alkylation cycle and a 24 hour regeneration cycle. The regeneration was with benzene. Very long runs were achieved by the alternating alkylation and regeneration cycles. During the alkylation cycle, samples were collected during the 6 to 12 hour run and the 18 to 24 hour run. The samples were then analyzed. By examining change between the two samples, a measure of the catalyst stability can be achieved. The first catalyst achieved complete olefin conversion as measured by the Bromine Index (BI) of less than 5 at 135° C., whereas the second catalyst was operated at 145° C. and had a BI ranging from 10 to 27. This was very close to full conversion. The reactor was operated at a pressure of about 3.5 MPa (500 psig) with an LHSV of 2.35 $hr^{-1}$. The results are shown in the following Table.

TABLE

Catalyst Results

| period | 1st Catalyst 6 to 12 | 1st Catalyst 18 to 24 | % of initial value | 2nd Catalyst 6 to 12 | 2nd Catalyst 18 to 24 | % of initial value |
|---|---|---|---|---|---|---|
| reactor inlet target T | 135 | 135 | | 145 | 145 | |
| Reactor 1 inlet T (° C.) | 134.1 | 134.0 | | 146 | 145.6 | |
| Rx cat. Tmax (° C.) | 136.4 | 136.2 | | 148 | 147.7 | |
| Bromine Index | <5 | <5 | | 10 | 27 | |
| total LAB | 87.95 | 88.02 | 100 | 85.82 | 83.36 | 97 |
| non-linear monoalkylate | 6.41 | 6.442 | 100 | 8.318 | 9.655 | 116 |
| linearity (%) | 93.21 | 93.18 | 100 | 91.16 | 89.62 | 98 |
| LAB/(LAB+HAB) (%) | 95.01 | 95.09 | 100 | 94.7 | 93.46 | 99 |
| total alkylate | 94.36 | 94.44 | 100 | 94.13 | 93.02 | 99 |
| 2-phenyl, total alkylate (%) | 26.1 | 29.0 | 111 | 24.6 | 28.6 | 116 |
| cracking | 1.019 | 1.017 | 100 | 1.063 | 1.146 | 108 |
| HAB/(HAB + AB + LAB) (%) | 4.67 | 4.59 | 98 | 4.9 | 5.9 | 122 |

As can be seen from the results, with the exception of the 2-phenyl content of the alkylate, the first catalyst exhibits very little change in product characteristics during the alkylation cycle. The comparison, or second, catalyst using the MOR zeolite shows significant changes in a number of properties of the product. With the comparison catalyst, the 2-phenyl concentration in the total alkylate changes more during the cycle, as does the amount of olefin isomerization. This is shown by the non-linear monoalkylate, which is an undesired product. The amount of heavies, usually dialkylbenzene (HAB), formed is also much larger with the second catalyst. And from the amount of olefin isomerization, the cracking is also higher with the second catalyst. The first catalyst produces a superior product, and is more stable over the alkylation cycle. This also shows that selection of zeolites for the multi-zeolite containing catalyst is not obvious as to the selection of the zeolites.

While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:

1. An alkylation process for the selective alkylation of an aromatic compound, comprising
contacting the aromatic compound with an olefin having from 8 to 16 carbon atoms in the presence of a selective zeolite catalyst at reaction conditions, wherein the selective zeolite catalyst comprises a zeolite mixture, the zeolite mixture comprising a first zeolite having a UZM-8 content between 10 and 90% by weight, a second zeolite comprising a rare earth substituted X zeolite, and comprising an amount between 10 and 90% by weight, wherein the reaction conditions include a temperature between 80° C. and 200° C. and a pressure between 1300 kPa and 7000 kPa, and the X zeolite has a silica to alumina ratio of less than 2.8;
and a rare earth element incorporated into the second zeolitic framework in an amount greater than 16.5 wt %.

2. The process of claim 1 wherein the reaction conditions include a temperature between 100° C. to 160° C.

3. The process of claim 1 wherein the reaction pressure is between 2500 and 4500 kPa.

\* \* \* \* \*